United States Patent
Saito et al.

(10) Patent No.: US 9,561,284 B2
(45) Date of Patent: Feb. 7, 2017

(54) PHARMACEUTICAL COMPOSITION CONTAINING A BLOCK COPOLYMER BOUND TO A BORONIC ACID COMPOUND

(75) Inventors: Hiroyuki Saito, Kashiwa (JP); Katsutoshi Kobayashi, Kashiwa (JP); Ryosuke Tanaka, Kashiwa (JP); Mitsunori Harada, Kashiwa (JP); Yasuki Kato, Kashiwa (JP)

(73) Assignee: NANOCARRIER CO., LTD., Kashiwa-shi (JP)

( * ) Notice: Subject to any disclaimer, the term of this patent is extended or adjusted under 35 U.S.C. 154(b) by 0 days.

(21) Appl. No.: 14/008,181

(22) PCT Filed: Apr. 2, 2012

(86) PCT No.: PCT/JP2012/058831
§ 371 (c)(1),
(2), (4) Date: Sep. 27, 2013

(87) PCT Pub. No.: WO2012/133884
PCT Pub. Date: Oct. 4, 2012

(65) Prior Publication Data
US 2014/0017192 A1    Jan. 16, 2014

(30) Foreign Application Priority Data
Mar. 31, 2011 (JP) ................................. 2011-080509

(51) Int. Cl.
*A61K 47/48* (2006.01)
*A61K 31/69* (2006.01)

(52) U.S. Cl.
CPC ......... *A61K 47/48207* (2013.01); *A61K 31/69* (2013.01); *A61K 47/48215* (2013.01); *A61K 47/48315* (2013.01)

(58) Field of Classification Search
None
See application file for complete search history.

(56) References Cited

U.S. PATENT DOCUMENTS

| | | | |
|---|---|---|---|
| 5,780,454 | A | 7/1998 | Adams et al. |
| 2008/0248097 | A1 | 10/2008 | Kwon et al. |
| 2010/0040556 | A1 | 2/2010 | Davis et al. |
| 2010/0221320 | A1 | 9/2010 | Kato et al. |
| 2010/0247669 | A1* | 9/2010 | Eliasof et al. ............. 424/501 |
| 2010/0298495 | A1 | 11/2010 | Bobe et al. |
| 2011/0142787 | A1 | 6/2011 | Nagasaki et al. |
| 2012/0283403 | A1 | 11/2012 | Matsumoto et al. |
| 2014/0017192 | A1 | 1/2014 | Saito et al. |

FOREIGN PATENT DOCUMENTS

| | | |
|---|---|---|
| JP | H05301880 A | 11/1993 |
| JP | H083172 A | 1/1996 |
| JP | 2002179683 A | 6/2002 |
| JP | 2010-519305 A | 6/2010 |
| JP | 2011140537 A | 7/2011 |
| JP | 2011173960 A | 9/2011 |
| WO | 96/13266 A1 | 5/1996 |
| WO | 2008/047948 A1 | 4/2008 |
| WO | 2009133647 A | 11/2009 |
| WO | 2010/013836 A1 | 2/2010 |
| WO | 2010/019718 A2 | 2/2010 |
| WO | 2012133884 A | 10/2012 |
| WO | 2013073697 A1 | 5/2013 |
| WO | WO2014021291 * | 8/2014 ............. A61K 9/127 |

OTHER PUBLICATIONS

Brown et al. (Stability of boronic esters structural effects on the relative rates of transesterification of 2-(phenyl)-1,3,2-dioxaborolane, Journal of Organometallic Chemistry, 2007, vol. 692, pp. 784-790).*
Matteson OL (A highly enantioselective and diastereoselective synthesis of cyclobutanes via boronic esters, Org. Lett. 1999, vol. 1, pp. 379-381).*
Matteson JOC (An efficient preparation of (R*, R*)-1,2-dicyclohexylethane-1,2-diol, a superior chiral director for synthesis with boronic esters, J. Org. Chem., 1996, vol. 61, pp. 8315-8316).*
Leroux et al., Polymeric micelle—a new generation of colloidal drug carriers, Eur. J. Pharm. and Biopharm., 1999, vol. 48, pp. 101-111.*
F. Nakanowatari et al., "Micelle formation from PEG-p(Lys) block copolymer with phenyl boronic acid moieties", Polymer Preprints, Japan, May 1999, vol. 48, No. 3, p. 572.
K. Kataoka, "Cellular specific material and new drug delivery system" Polyfile, Apr. 1993, pp. 27-31.
L. Zhao et al., "Glucose-sensitive polypeptide micelles for self-regulated insulin release at physiological pH", J. Mater. Chem., 2012, vol. 22, pp. 12319-12328.
M. Naito et al., "Design and physicochemical evaluation of novel polymeric micelle forming reversible covalent bond with ribose for siRNA delivery carrier", Polymer Preprints, Japan, May 2012, vol. 61, No. 1, p. 1642.

(Continued)

*Primary Examiner* — Bethany Barham
*Assistant Examiner* — Ping Cao
(74) *Attorney, Agent, or Firm* — J-Tek Law PLLC; Jeffrey Tekanic; Scott Wakeman

(57) ABSTRACT

A pharmaceutical composition includes a block copolymer having a hydrophilic segment, a hydrophobic segment, and a boronic acid compound bound to a side chain of the hydrophobic segment via a linker moiety that includes a heterocyclic structure. The heterocyclic structure contains a cyclic skeleton that includes a boron atom of the boronic acid compound, one or two atom(s) X bound to the boron atom and selected from an oxygen atom and a nitrogen atom, and one or two carbon atom(s) (respectively) bound to the atom(s) X. The block copolymer further includes at least one organic group bound to the carbon atom(s). The organic group(s) contain(s) an aromatic group or cyclic alkyl group that sterically protects a boronic acid ester bond and/or a boron amide bond resulting from bonding between the boron atom and the atom(s) X.

3 Claims, 3 Drawing Sheets

(56) References Cited

OTHER PUBLICATIONS

US un-published U.S. Appl. No. 14/358,816.
English translation of International Preliminary Report on Patentability from parent International application No. PCT/JP2012/058831.
Extended European Search Report dated Oct. 6, 2014 for counterpart EP application No. 12765657.7, including European Search Opinion, Supplementary European Search Report and examined claims 1-7.
Martin Piest: "Boronic Acid Functionalized Polymers and Hydrogels for Biomedical Applications", Sep. 30, 2011, pp. 111-114 (Chapter 6 of Dissertation), XP002729858.
English translation of International Search Report from parent application No. PCT/JP2012/058831.

* cited by examiner

PHARMACEUTICAL COMPOSITION CONTAINING A BLOCK COPOLYMER BOUND TO A BORONIC ACID COMPOUND

CROSS-REFERENCE

This application is the US national stage of International Patent Application No. PCT/JP2012/058831 filed on Apr. 2, 2012, which claims priority to Japanese Patent Application No. 2011-080509 filed on Mar. 31, 2011.

TECHNICAL FIELD

The present invention generally relates to a pharmaceutical composition including a block copolymer bound to a boronic acid compound such as Velcade® (generic name: bortezomib).

BACKGROUND ART

Boronic acid compound are expected to find use in a variety of medical applications. For example, bortezomib is known as a potent anti-cancer agent that suppresses the growth of myeloma cells by inhibiting the action of an enzyme (proteasome) that degrades unnecessary proteins in cells and by inhibiting the activation of NF-κB. The proteasome is a biological mechanism for degrading structurally abnormal proteins or surplus proteins. Cell growth rate is extremely high in cancer cells as compared to normal cells, and protein synthesis is carried out more actively in cancer cells than in normal cells, resulting in an increased synthesis amount of structurally abnormal proteins as well. Therefore, the function of the proteasome is inhibited by bortezomib and the intracellular concentration of abnormal proteins increases. Further, the activation of NF-κB plays important roles in the survival, growth, and infiltration of tumor cells. NF-κB is generally present as an inactive form while it is bound to its inhibitory protein IκBα. NF-κB is activated by degradation of IκBα by the proteasome. The activation of NF-κB is inhibited by bortezomib inhibiting the function of the proteasome. These phenomena caused by bortezomib can lead to dysfunction and cell death of cancer cells. However, the proteasome is present in normal cells as well, and hence bortezomib has severe side effects. For example, myelosuppression, lung disorder, tumor lysis syndrome, gastrointestinal disorders, peripheral neuropathy, pneumonia, and cardiovascular disorders have been reported as side effects.

The inventors of the present invention have advanced the development of a drug delivery system (DDS) using a polymer micelle from the viewpoint of enhancing the efficacy of a drug while reducing the side effects thereof. One of the goals of the DDS resides in achieving a sustained release of a drug through micelle formation, i.e. the stable retention of a drug in a micelle under physiological conditions, to thereby prevent an abrupt rise in the concentration of the drug in blood and avoid the occurrence of side effects.

However, a polymer micelle capable of sufficiently stably retaining a boronic acid compound such as bortezomib under physiological conditions or a block copolymer suitable for forming the polymer micelle has not yet been achieved. It should be noted that the following references are prior art relating to boronic acid compounds.

CITATION LIST

Patent Literature

[Patent Literature 1] WO 96/13266 A1
[Patent Literature 2] U.S. Pat. No. 5,780,454 B
[Patent Literature 3] WO 2010/019718 A1
[Patent Literature 4] US 2010/0247669 A1

SUMMARY OF THE INVENTION

In one aspect of the present teachings, a polymer micelle is disclosed that is capable of stably retaining a boronic acid compound such as bortezomib under physiological conditions, so that it may be used as a pharmaceutical composition. A block copolymer composition suitable for forming the polymer micelle is also disclosed.

The present inventors found that, when a boronic acid compound is bound to a hydrophobic segment of a block copolymer via a specific chemical structure, the boronic acid compound can be much retained more stably under physiological conditions due to micelle formation. More particularly, a pharmaceutical composition preferably includes a block copolymer having: a hydrophilic segment, a hydrophobic segment, and a boronic acid compound bound to a side chain of the hydrophobic segment via a linker moiety that includes a heterocyclic structure. The cyclic skeleton of the heterocyclic structure contains a boron atom originating from the boronic acid compound, (an) atom(s) (X) bound to the boron atom and selected from an oxygen atom and a nitrogen atom, and (a) carbon atom(s) bound to the atom(s) (X). The block copolymer further has one or more organic group(s) bound to the carbon atom(s), the organic group(s) containing an aromatic group or cyclic alkyl group as a structure that protects a boronic acid ester bond and/or a boron amide bond resulting from bonding between the boron atom and the atom(s) (X).

According to one embodiment of the present invention, the stable retention property of the boronic acid compound under physiological conditions in a polymer micelle type DDS can be improved.

MODES FOR CARRYING OUT THE INVENTION

A. Pharmaceutical Composition

Figure 1:
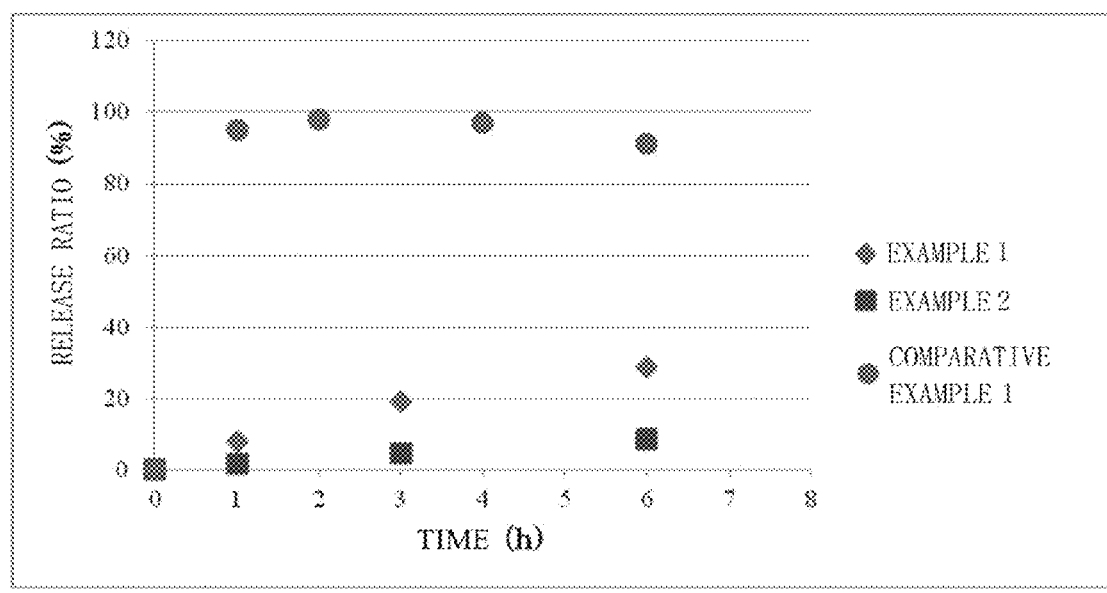
FIG. 1 is a graph showing drug release test results of polymer micelle compositions formed of block copolymer compositions of Example 1, Example 2, and Comparative Example 1.

Pharmaceutical compositions of the present invention include a block copolymer having: a hydrophilic segment, a hydrophobic segment, and a boronic acid compound bound to a side chain of the hydrophobic segment via a linker moiety that includes a heterocyclic structure. The block copolymer has, in its linker moiety, a specific chemical structure that protects the bond(s) to the boronic acid compound, and thus is capable of stably retaining the boronic acid compound under physiological conditions in a form of, for example, a polymer micelle.

Specifically, the cyclic skeleton of the heterocyclic structure has a boron atom originating from the boronic acid compound, (an) atom(s) X bound to the boron atom and selected from an oxygen atom and a nitrogen atom, and (a) carbon atom(s) bound to the atom(s) X. The carbon atom(s) is (are) bound to (an) organic group(s) containing an aromatic group or cyclic alkyl group as a structure that protects a boronic acid ester bond and/or a boron amide bond resulting from bonding between the boron atom and the atom(s) X.

More specifically, the cyclic skeleton of the heterocyclic structure has a boron atom originating from the boronic acid compound, atoms $X^1$ and $X^2$ bound to the boron atom and each independently selected from an oxygen atom and a nitrogen atom, a carbon atom bound to atom $X^1$, and a carbon atom bound to atom $X^2$. At least one of the carbon atom bound to atom $X^1$ and the carbon atom bound to atom $X^2$ is bound to the organic group containing the aromatic group or cyclic alkyl group as the structure that protects a boronic acid ester bond and/or a boron amide bond resulting from bonding between the boron atom and atoms $X^1$ and $X^2$.

In a preferred embodiment of the present invention, the heterocyclic structure may be represented by the following chemical structure (I) or (II):

[Chem. 1]

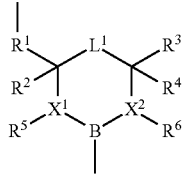
(I)

[Chem. 2]

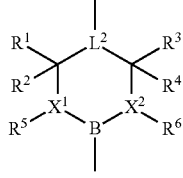
(II)

where:
B represents the boron atom originating from the boronic acid compound;
at least one of $R^1$, $R^2$, $R^3$, and $R^4$ represents the organic group;
$X^1$ and $X^2$ each independently represent an oxygen atom or a nitrogen atom;
$R^5$ and $R^6$ each independently represent hydrogen or a substituted or unsubstituted alkyl group having 1 to 6 carbon atoms, provided that $R^5$ and $R^6$ are absent when $X^1$ and $X^2$ each represent an oxygen atom;
$L^1$ represents —$(CH_2)_{p1}$— (where p1 represents an integer of 0 to 5) ; and $L^2$ represents —$(CH_2)_{p2}$-M-$(CH_2)_{p3}$— (where M represents CH or N and p2 and p3 each independently represent an integer of 0 to 2).

As was described above, at least one of $R^1$, $R^2$, $R^3$, and $R^4$ represents an organic group containing an aromatic group or cyclic alkyl group as the structure that protects a boronic acid ester bond and/or a boron amide bond (hereinafter sometimes simply referred to as "the protective structure"). The aromatic group or cyclic alkyl group as the protective structure is desirably disposed in proximity to (a) carbon atom(s) constituting the cyclic skeleton of the heterocyclic structure in at least one of $R^1$, $R^2$, $R^3$, and $R^4$. Specifically, the protective structure(s) is (are) bound to (a) carbon atom(s) constituting the cyclic skeleton of the heterocyclic structure preferably via 1 to 4 atoms or directly, more preferably via 1 or 2 atoms or directly, still more preferably via 1 atom or directly. More specifically, an aromatic ring (aromatic ring originating from the aromatic group) or a cycloalkyl ring (cycloalkyl ring originating from the cyclic alkyl group) in the protective structure is bound to (a) carbon atom(s) constituting the cyclic skeleton of the heterocyclic structure preferably via 1 to 4 atoms or directly, more preferably vial or 2 atoms or directly, still more preferably via 1 atom or directly. The stable retention property of the boronic acid compound can be suitably improved by disposing (a) bulky ring structure(s) in proximity to the boronic acid ester bond and/or the boron amide bond.

A phenyl group, a benzyl group, a naphthyl group, an anthracenyl group, a biphenyl group, and a triphenyl group can be given as specific examples of the aromatic group. Further, a cycloalkyl group having 3 to 10 carbon atoms can be given as a specific example of the cyclic alkyl group. A plurality of (e.g., two or three) cycloalkyl groups may be linked together. These aromatic groups and cyclic alkyl groups may be substituted with any appropriate substituent. An alkyl group (more specifically, a linear or branched alkyl group having 1 to 4 carbon atoms), a halogen, a cyano group, a formyl group, a carboxyl group, an amino group, an alkoxycarbonyl group, an acylamide group, a siloxy group, a tri(alkyl) siloxy group, and a silylamino group can be given as specific examples of the substituent. The aromatic group is preferably a phenyl group or a benzyl group. The cyclic alkyl group is preferably a cyclopentyl group or a cyclohexyl group.

The protective structure is preferably contained in two or more of $R^1$, $R^2$, $R^3$, and $R^4$. In one embodiment, two of any one of $R^1$ and $R^2$ and any one of $R^3$ and $R^4$ represent an aromatic group (e.g., a phenyl group or a benzyl group).

Groups containing no protective structure from among $R^1$, $R^2$, $R^3$, and $R^4$ may each independently be a linear or branched alkyl group having 1 to 16, for example, 1 to 12, or for example, 1 to 8, or for example, 1 to 4 carbon atoms. Further, the groups containing no protective structure from among $R^1$, $R^2$, $R^3$, and $R^4$ may be hydrogen atoms for groups except $R^1$ in the above-mentioned chemical structure (I), but are preferably linear alkyl groups each having 1 or more carbon atoms or branched alkyl groups each having 3 or more carbon atoms, from the viewpoint of reinforcing the protection of the boronic acid ester bond and/or the boron amide bond. It should be noted that, for $R^1$ in chemical structure (I), the aromatic group, the cyclic alkyl group, and the linear or branched alkyl group mean residues originating from these groups.

Atoms $X^1$ and $X^2$ are each independently selected from an oxygen atom or a nitrogen atom, and are bound to the boron atom to form a boronic acid ester bond or a boron amide bond. Valence electrons of nitrogen more easily enter the empty p-orbital of the boron atom than valence electrons of oxygen. Hence, the boron amide bond has a higher stability than the boronic acid ester bond, and is thus considered to be advantageous from the viewpoint of the stable retention property of the boronic acid compound.

$R^5$ and $R^6$ each independently represent hydrogen or a substituted or unsubstituted alkyl group having 1 to 6 carbon atoms when $X^1$ and/or $X^2$ represent(s) a nitrogen atom. A halogen, a cyano group, a formyl group, a carboxyl group, an amino group, an alkoxycarbonyl group, an acylamide group, a siloxy group, a tri(alkyl) siloxy group, and a silylamino group can be given as examples of the substituent.

$L^1$ represents $-(CH_2)_{p1}-$ where p1 preferably represents 0 or 1. Further, $L^2$ represents $-(CH_2)_{p2}-M-(CH_2)_{p3}$ where M represents CH or N and p2 and p3 preferably each independently represent 0 or 1.

In a more preferred embodiment of the present invention, the heterocyclic structure is at least one selected from the group consisting of the following chemical structures (III) to (V):

[Chem. 3]

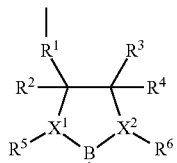
(III)

[Chem. 4]

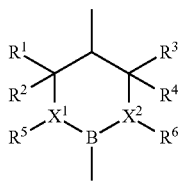
(IV)

[Chem. 5]

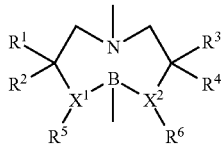
(V)

where B, $R^1$ to $R^6$, $X^1$, and $X^2$ in each of chemical structures (III) to (V) are as defined in the above-mentioned chemical structure (I) or (II).

The hydrophilic segment in the block copolymer is formed of a hydrophilic polymer chain. Any appropriate hydrophilic polymer may be utilized as the hydrophilic polymer. Polyethylene glycol, a polysaccharide, polyvinylpyrrolidone, polyvinyl alcohol, polyacrylamide, polyacrylic acid, polymethacrylamide, polymethacrylic acid, polymethacrylate, polyacrylate, a polyamino acid, polymalic acid, and derivatives thereof can be given as specific examples of the hydrophilic polymer. Starch, dextran, fructan, and galactan can be given as specific examples of the polysaccharide. Polyethylene glycol is preferred. This is because end-reactive polyethylene glycols having a variety of functional groups at their ends are commercially available and polyethylene glycols having various molecular weights are also commercially available; hence polyethylene glycols having properties appropriate for the objective are readily available.

The hydrophobic segment in the block copolymer is formed of a hydrophobic polymer chain. Any appropriate hydrophobic polymer may be utilized as the hydrophobic polymer. Polyamino acid chains of polyglutamic acid, polyaspartic acid, and ester or amide derivatives thereof can be given as specific examples of the hydrophobic polymer. Such ester or amide derivatives can be formed by subjecting a corresponding hydroxy compound or amino compound having a hydrophobic organic group to a reaction with a reactive derivative (e.g., an ester) of polyglutamic acid or polyaspartic acid. An alkyl phenyl group whose alkyl group has 1 to 6 carbon atoms, cholesterol, and an alkyl group having 8 to 18 carbon atoms can be given as specific examples of the hydrophobic organic group. A poly(β-alkyl aspartate-co-aspartic acid), poly(β-allyl aspartate-co-aspartic acid), a poly(β-aralkyl aspartate-co-aspartic acid), a poly(γ-alkyl glutamate-co-glutamic acid), a poly(γ-aralkyl glutamate-co-glutamic acid), a poly(β-alkyl aspartamide-co-aspartic acid), a poly(γ-aralkyl glutamide-co-glutamic acid), poly(β-benzyl-L-aspartate), and poly(γ-benzyl-L-glutamate) can be give as specific examples of the derivatives.

The introduction ratio of the protective structures into the side chains of the hydrophobic segment may be, for example, 50% or more, or for example, 60% or more, or for example, 70% or more, or for example, 90% or more when one of the groups $R^1$, $R^2$, $R^3$, and $R^4$ contains the protective structure. When two or more of the groups $R^1$, $R^2$, $R^3$, and $R^4$ each contain the protective structure, the introduction ratio may be adjusted to less than 50%, for example, less than 40%, or for example, less than 30% depending on the increase in the steric hindrance associated with the incorporation of such bulky structures. It is considered that the increase in the steric hindrance in the vicinity of the bond to the boronic acid compound through the introduction of the protective structure inhibits the access of water molecules to the bond, which would result in the cleavage of the bond, to thereby improve the stable retention property of the boronic acid compound under physiological conditions. It should be noted that, if a linear structure is introduced instead of the protective structure, it is not possible to significantly improve the stable retention property of the boronic acid compound.

In one embodiment, the block copolymer is represented by the following formula (1) or (2). It should be noted that the "block copolymer" as used herein also encompasses pharmaceutically acceptable salts of the block copolymer.

[Chem. 6]

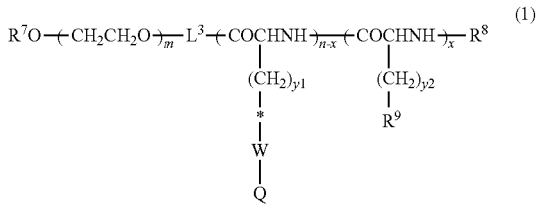
(1)

[Chem. 7]

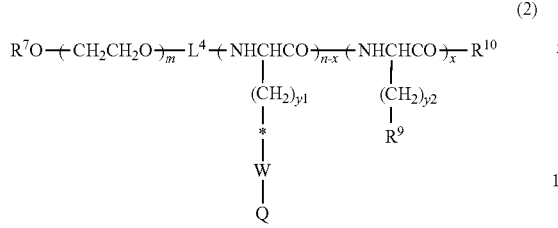
(2)

In formulas (1) and (2), $R^7$'s each independently represent a hydrogen atom, a methyl group, or a linear, branched, or cyclic $C_1$ to $C_{12}$ alkyl group that may have a substituent. An acetalated formyl group, a cyano group, a formyl group, a carboxyl group, an amino group, a $C_1$ to $C_6$ alkoxycarbonyl group, a $C_2$ to $C_7$ acylamide group, a siloxy group having three $C_1$ to $C_6$ alkyl groups identical to or different from each other, a siloxy group, a silylamino group, a maleimide group, a thiol group, a hydroxyl group, and an active ester group can be give as examples of the substituent. Such a substituent may be protected by any appropriate protective group. $R^8$ represents a hydrogen atom, a saturated or unsaturated $C_1$ to $C_{30}$ aliphatic carbonyl group, or a $C_6$ to $C_{30}$ arylcarbonyl group. $R^9$'s each independently represent a hydroxyl group, an amino group, an acylamino group, a carboxyl group, or a carboxylic acid ester (e.g., a benzyl ester or a $C_1$ to $C_6$ alkyl ester) for the respective repeating units. $R^{10}$ represents a hydroxyl group, a saturated or unsaturated $C_1$ to $C_{30}$ aliphatic oxy group, or a $C_6$ to $C_{30}$ aryl-lower alkyloxy group. $L^3$ and $L^4$ each independently represent a linking group. m represents an integer of 5 to 20,000, n represents an integer of 2 to 5,000, and x represents an integer of 0 to 5,000 (provided that the integer x is smaller than the integer n), $y_1$ represents an integer of 0 to 5, and $y_2$ represents an integer of 1 to 5. W represents a heterocyclic structure represented by chemical structure (I) or (II). Q represents a residue of a boronic acid compound. The mark * represents a single bond or a divalent linking group. It should be noted that details of the boronic acid compound and a method of introducing the boronic acid compound into the block copolymer will be described below.

Preferably, m represents an integer of 5 to 20,000, more preferably an integer of 10 to 5,000, particularly preferably an integer of 40 to 500. Preferably, n represents an integer of 2 to 5,000, more preferably an integer of 10 to 100, still more preferably an integer of 20 to 80, particularly preferably an integer of 30 to 50, most preferably an integer of about 40. Thus, the term "poly (polymer)" as used herein encompasses a so-called "oligo (oligomer)." Further, these numerical values mean average values (peak values) of molecular weight distributions.

x defines the introduction ratio of the boronic acid compound into the side chains of the hydrophobic segment in the block copolymer. As described above, x preferably represents an integer of 0 to 5,000 (provided that the integer x is smaller than the integer n). When x is not 0, the sequence of the respective repeating units may be random, alternating, block, or combinations thereof. The ratio of n-x to n (i.e., the introduction ratio of the boronic acid compound into the side chains of the hydrophobic segment) may be, for example, 50% or more, or for example, 60% or more, or for example, 70% or more, or for example, 90% or more when one of $R^2$, $R^2$, $R^3$, and $R^4$ contains the protective structure, and may be less than 50%, for example, less than 40%, or for example, less than 30% when two or more of $R^2$, $R^2$, $R^3$, and $R^4$ each contain the protective structure.

Any appropriate linking group may be utilized as each of the linking groups $L^3$ and $L^4$ as long as it can link together a hydrophilic segment (e.g., a polyethylene glycol chain) and a hydrophobic segment (e.g., a polyamino acid chain). Specific examples of the linking group $L^3$ include —$(CH_2)_b$—NH—. In the formula, b represents an integer of 1 to 5. Specific examples of the linking group $L^4$ include —$(CH_2)_c$—CO—. In the formula, c represents an integer of 1 to 5.

The structure W is preferably selected from the heterocyclic structures represented by chemical structures (III) to (V). Each of the structures W's may be independently selected for the respective repeating units.

For example, when W is chemical structure (I), the mark * may represent a single bond. Further, for example, when W is chemical structure (II), the mark * may represent a divalent linking group. Divalent linking groups having 0 to 5 carbon atoms, which may include an amide bond, an ester bond, an ether bond, and the like, can be given as examples of the divalent linking group. More specific examples thereof include —$(CH_2)_d$—, —NHCO—, —CONH—, —COO—, —O—, —CO—, and combinations thereof. In the formula, d represents an integer of 1 to 5, preferably 1 or 2.

The boronic acid compound may be any appropriate compound having a boronic acid group. The boronic acid compound is typically represented by the following formula (3):

[Chem. 8]

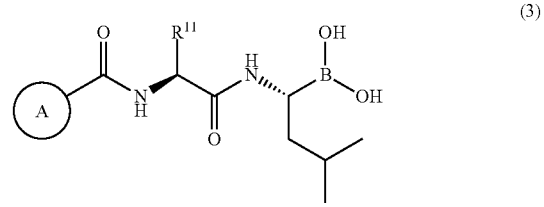
(3)

where $R^{11}$ represents a hydrogen atom, a linear or branched alkyl group having 1 to 16 carbon atoms, or an aromatic group, preferably a hydrogen atom, a benzyl group, a phenyl group, more preferably a benzyl group, and ring A is a heterocycle. Specific examples of the heterocycle include a pyridiyl group, a pyrimidyl group, a furanyl group, a thienyl group, a pyrrolyl group, a pyrazolyl group, an imidazolyl group, a tetrazolyl group, a benzofuranyl group, a benzothiophenyl group, an indolyl group, an indolenyl group, a quinolinyl group, an isoquinolinyl group, a benzimidazolyl group, a piperidinyl group, a pyrrolidinyl group, a 2-pyrrolidonyl group, a pyrrolinyl group, a tetrahydrofuranyl group, a tetrahydroquinolinyl group, a tetrahydroisoquinolinyl group, a decahydroquinolinyl group, an octahydroisoquinolinyl group, an azocinyl group, a triazinyl group, a 6H-1,2,5-thiazinyl group, a 2H, 6H-1,5,2-dithiazinyl group, a thiophene(yl) group, a thianthrenyl group, a furanyl group, a pyranyl group, an isobenzofuranyl group, a chromenyl group, a xanthenyl group, a phenoxathiinyl group, a 2H-pyrrolyl group, a pyrrole group, an imidazolyl group, a pyrazolyl group, an isothiazolyl group, an isoxazolyl group, a pyridinyl group, a pyrazinyl group, a pyrimidinyl group, a pyridazinyl group, an indolizinyl group, an isoindolyl group, a 3H-indolyl group, an indolyl group, a 1H-indazolyl group, a purinyl group, a 4H-quinolizinyl group, an isoquinolinyl group, a quinolinyl group, a phthalazinyl group, a naphthyridinyl group, a quinoxalinyl group, a quinazolinyl group, a cinnolinyl group, a pteridinyl group, a 4aH-carbazolyl group, a carbazolyl group, a β-carbolinyl group, a phenanthridinyl group, an acridinyl group, a phenanthrolinyl group, a phenazinyl group, a phenothiazinyl group, a furazanyl group, a phenoxazinyl group, an isochromanyl group, a chromanyl group, a pyrrolidinyl group, an imidazolidinyl group, an imidazolinyl group, a pyrazolidinyl group, a pyrazolinyl group, a piperazinyl group, an indolinyl group, an isoindolinyl group, a quinuclidinyl group, a morpholinyl group, and an oxazolidinyl group. A pyrazinyl group is preferred.

The boronic acid compound is particularly preferably bortezomib (formula (3) where $R^{11}$ represents a benzyl group and ring A is a pyrazinyl group). The reason for this is as described below. According to one embodiment of the present invention, when the boronic acid compound is bound to the block copolymer via a linker moiety having the protective structure, the retention property of the boronic acid compound under physiological conditions is remarkably improved. As a result, for bortezomib, which is known to have severe side effects from among the boronic acid compounds, the effect of reducing its side effects is large, and thus the advantage of the present invention becomes remarkable.

A method of introducing a boronic acid compound into a side chain of a hydrophobic segment of a block copolymer having a hydrophilic segment and a hydrophobic segment via a linker moiety that includes a heterocyclic structure represented by the chemical structure (III) is described below. For simplicity, a method of introducing bortezomib into a block copolymer having polyethylene glycol as the hydrophilic segment and polyglutamic acid as the hydrophobic segment is described as an example. The introduction of bortezomib is carried out according to the following reaction scheme:

[Chem. 9]

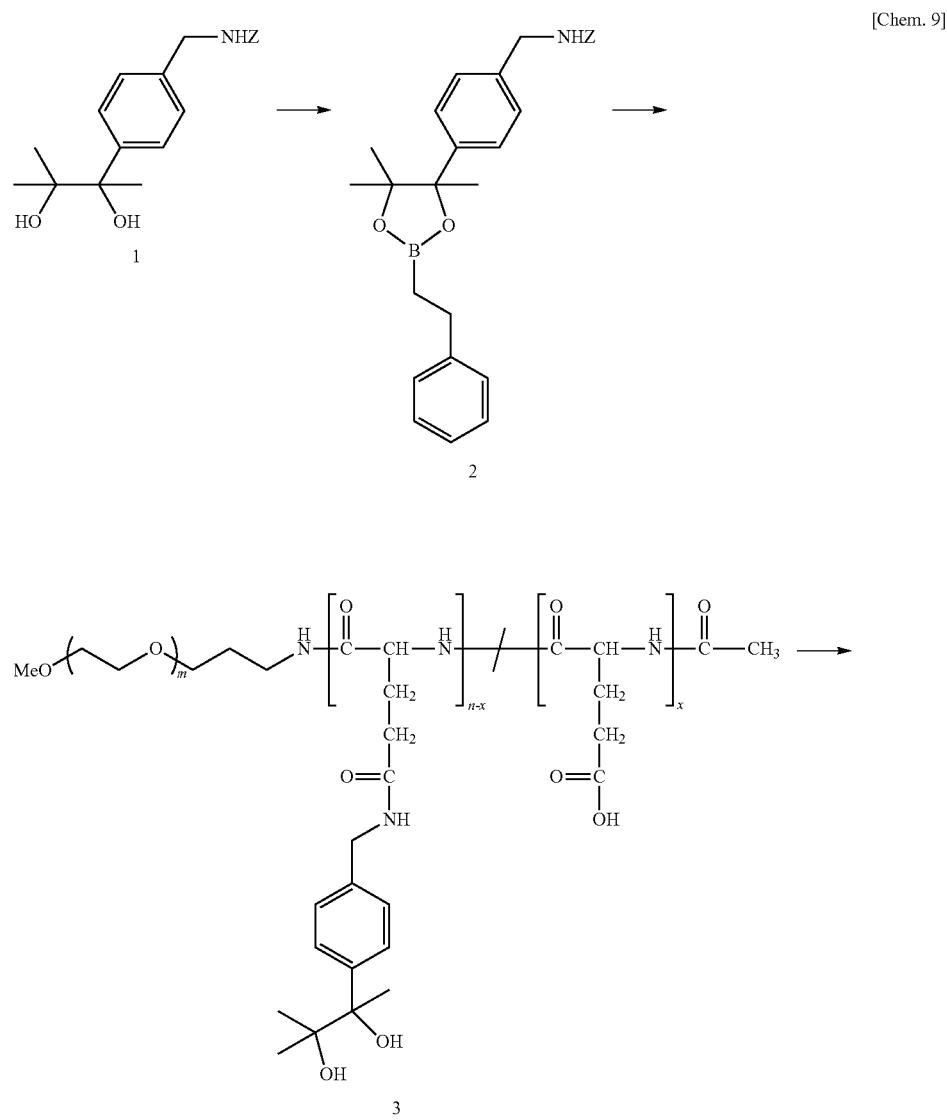

-continued

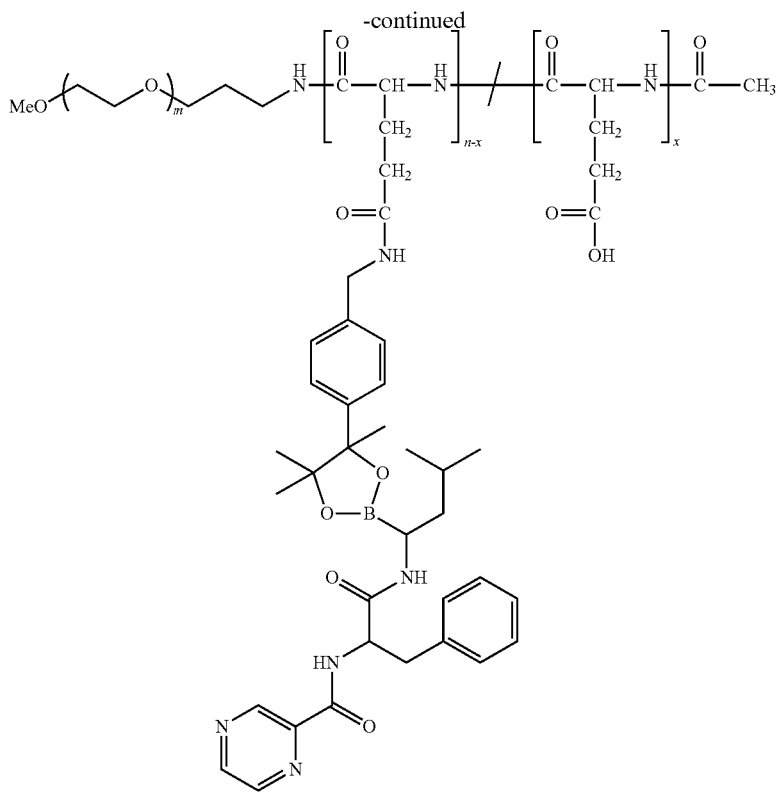

4

First, compound 1 is obtained by any appropriate method. It should be noted that Z in compound 1 represents any appropriate protective group. Compound 1 is subjected to a dehydration reaction with phenethylboronic acid to protect the hydroxyl groups of compound 1, thereby yielding compound 2. Next, compound 2 is subjected to a reaction with a block copolymer of polyethylene glycol and polyglutamic acid. Specifically, water is eliminated through a reaction between a carboxyl group of a side chain of a polyglutamic acid block and an amino group of compound 2. Then, deprotection is carried out by alkali treatment to yield copolymer 3. Finally, copolymer 3 is subjected to a dehydration reaction with bortezomib to yield block copolymer 4 having a protective structure for a boronic acid ester bond (block copolymer contained in the pharmaceutical composition of the present invention). The introduction ratio of the boronic acid compound (e.g., bortezomib) in the block copolymer is, for example, 50% or more, or for example, 60% or more, or for example, 70% or more, or for example, 90% or more. It should be noted that, in this description, "/" shown between the repeating units of the structural formula of the copolymer means that the sequence of these repeating units is arbitrary and may be, for example random, alternating, block, or combinations thereof.

B. Polymer Micelle Composition

According to another aspect of the present invention, a polymer micelle composition can be provided. The polymer micelle composition of the present invention includes the block copolymer described in the above-mentioned section A, and may be suitably used as an anti-tumor composition. Block copolymers can undergo association in an aqueous solution to suitably form micelle particles. The micelle particles each have an average particle diameter of, for example, 5 nm to 5 μm, preferably 5 to 500 nm, more preferably 10 to 300 nm.

EXAMPLES

Hereinafter, the present invention is more specifically described by way of examples. However, the present invention is not limited by these examples.

Example 1

According to the above-mentioned reaction scheme, bortezomib was introduced into a block copolymer of polyethylene glycol and polyglutamic acid via a linker moiety that includes the heterocyclic structure represented by chemical structure (III). The introduction is specifically described below.

<1. Synthesis of Compound 2>

Compound 1 (430 mg, 1.25 mmol) was dissolved in THF (10 mL) and subjected to a reaction with phenethylboronic acid (376 mg, 0.25 mmol) at room temperature in the presence of molecular sieves 4A and p-toluenesulfonic acid monohydrate (50 mg, 0.26 mmol). After 2 hours, the completion of the reaction was confirmed by TLC, the molecular sieves were separated by filtration, and then the filtrate was concentrated under reduced pressure. The resultant residue was dissolved in ethyl acetate (50 mL), washed with a saturated sodium bicarbonate aqueous solution (50 mL×3) and brine (50 mL×3), dried over anhydrous magnesium sulfate, and concentrated.

The residue was purified by silica gel chromatography {eluent: hexane/ethyl acetate=5/2(v/v)} to yield compound 2 (515 mg, yield: 89.9%) as a colorless oily product.

$^1$H NMR (CDCl$_3$) δ: 0.70 (3H, s), 1.28 (2H, t, J=8.0 Hz), 1.46 (3H, s), 1.48 (3H, s), 2.84 (2H, t, J=8.0 Hz), 4.37 (2H, d, J=5.9 Hz), 5.06 (1H, br s), 5.14 (2H, s), 7.13-7.35 (14H, m)

<2. Synthesis of Block Copolymer 3>

Compound 2 (515 mg, 1.13 mmol) was dissolved in ethanol (20 mL), and hydrogen gas was blown into the solution in the presence of 10% palladium carbon (50 mg). After the completion of the reaction, the palladium carbon was separated by filtration, and the filtrate was concentrated under reduced pressure. The residue was subjected to a reaction with a separately synthesized block copolymer of polyethylene glycol and polyglutamic acid (355 mg, 0.023 mmol, average molecular weight of polyethylene glycol: 10 kDa, average polymerization degree of polyglutamic acid: 40, average molecular weight of block copolymer: 15,200) through the use of N,N-diisopropylcarbodiimide (146 µL, 0.94 mmol) and 4-dimethylaminopyridine (114 mg, 0.93 mmol) in dry DMF (5 mL) under an argon atmosphere for 3 days. After the reaction, the reaction liquid was crystallized with a mixed solvent (100 mL) of hexane and ethyl acetate {hexane/ethyl acetate=1/1 (v/v)}, and the precipitated polymer was filtered by suction. The polymer powder collected by the filtration was dispersed in the same solvent as described above, washed, and filtered by suction. The same operation was carried out once more, and the resultant polymer powder was dried under reduced pressure at room temperature overnight.

The resultant polymer was treated with a 0.5 N sodium hydroxide aqueous solution (3 mL), and the alkali was removed by dialysis (molecular weight cut-off: 1,000) treatment. After that, a 0.5 N hydrochloric acid aqueous solution (3 mL) was added, and the dialysis treatment was continued. After the removal of the acid, the polymer aqueous solution was collected and lyophilized to yield block copolymer 3 (520 mg) to which a linker was bound. The number of linker molecules introduced was 29 molecules per molecule of the block copolymer based on $^1$H NMR spectrum analysis.

<3. Synthesis of Block Copolymer Composition 4>

The resultant block copolymer 3 (100 mg, 4.83×10$^{-3}$ mmol) was dissolved in dry DMF (2 mL) under an argon atmosphere and subjected to a reaction with bortezomib (58.9 mg, 0.153 mmol) in the presence of molecular sieves 4 A and p-toluenesulfonic acid monohydrate (5.5 mg, 0.029 mmol) at room temperature for an entire day and night. After the reaction, the reaction liquid was crystallized with a mixed solvent (50 mL) of hexane and ethyl acetate {hexane/ethyl acetate=1/1 (v/v)}, and the precipitated polymer was filtered by suction. The polymer powder collected by the filtration was dispersed in the same solvent (50 mL) as described above, washed, and filtered by suction. This operation was carried out once more, and the resultant polymer powder was dried under reduced pressure at room temperature overnight to yield block copolymer composition 4 (95 mg) in which bortezomib was bound via a protective structure for a boronic acid ester bond, as the pharmaceutical composition of the present invention. The number of bortezomib molecules introduced was 29 molecules per molecule of the block copolymer based on $^1$H NMR spectrum analysis.

Comparative Example 1

Aspartic acid side chains of a block copolymer of polyethylene glycol and polyaspartic acid-β-benzyl ester (1.72 g, 0.095 mmol, average molecular weight of polyethylene glycol: 10 kDa, average polymerization degree of polyaspartic acid: 40, average molecular weight of block copolymer: 18,200) were bound to bortezomib via a predetermined linker moiety to yield block copolymer composition 5 (90 mg) shown below. The number of bortezomib molecules introduced was 15 molecules per molecule of the block copolymer based on $^1$H NMR spectrum analysis.

[Chem. 10]

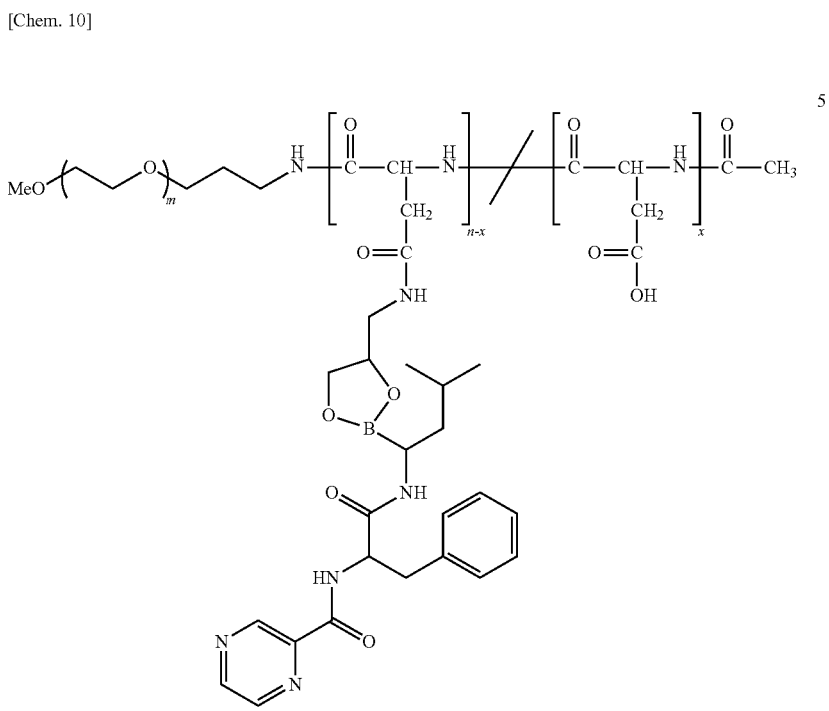

Example 2

Glutamic acid side chains of a block copolymer of polyethylene glycol and polyglutamic acid (680 mg, 0.045 mmol, average molecular weight of polyethylene glycol: 10 kDa, average polymerization degree of polyglutamic acid: 40, average molecular weight of block copolymer: 15,200) were bound to bortezomib via a predetermined linker moiety to yield block copolymer composition 6 (320 mg) shown below as a pharmaceutical composition of the present invention. The number of bortezomib molecules introduced was 9.5 molecules per molecule of the block copolymer based on $^1$H NMR spectrum analysis.

[Chem. 11]

[Structure 6: block copolymer of MeO-PEG with polyglutamic acid side chains linked to bortezomib]

HPLC Conditions:
System: HITACHI Inter-face D-7000 (L-7100, L-7200, L-7300, L-7405)
Column: Waters XTerra™ MSC18 (4.6×100 mm, 3.5 μm)
Mobile phase: A (water:acetonitrile:formic acid=7:3:0.1), B (water:acetonitrile:formic acid=2:8:0.1)
Gradient: 0 (100), 15 (100), 20 (0), 32 (0), 34 (100), 40 (100) min (A %)
Column temperature: 35° C.
Flow rate: 1 mL/min
Injection volume: 10 μL
Measurement time: 40 min <Drug Release Test>

1. Preparation of Sample Solution

Ultrapure water was added to the block copolymer composition in which bortezomib was bound obtained in each of Examples and the Comparative Example so as to achieve a block copolymer composition concentration of 1.0 mg/mL. The mixture was stirred at room temperature for 10 minutes and then ultrasonicated under cooling with ice water for 10 minutes to prepare a sample solution.

2. Measurement of Bortezomib Content

500 μL of 2.0 N NaOH were added to 500 μL of the sample solution (as a result, block copolymer composition concentration: 0.5 mg/mL, alkali concentration: 1.0N), and the mixture was incubated under light shielding at 37° C. and then 200 μL thereof were fractionated. 200 μL of 1.0 N HCl were added to neutralize and dilute the fraction (as a result, block copolymer composition concentration: 0.25 mg/mL), and the bortezomib content was measured under the following HPLC conditions.

Detection: UV 270 nm
Retention time of bortezomib: 4.6 min

3. Release Test

To 1.0 mL of the sample solution was added 1.0 mL of a 200 mM sodium phosphate buffer (pH 7.4), and the mixture was stirred. After that, 350 μL of the mixture were fractionated for each of measurements, and incubated under light shielding at 37° C. for each measurement time (0, 1, 3, 6, or 24 hours). After that, 200 μL thereof were fractionated, 200 μL of ultrapure water were added to the fraction, and the amount of bortezomib released was measured under the above-mentioned HPLC conditions. The drug release ratio was calculated with the following calculation equation.

Drug release ratio (%)={(Amount of bortezomib released)/(Total amount of bortezomib)}×100

FIG. 1 shows the relationship between the elapsed time after the preparation of the sample solution and the drug release ratio. As is apparent from FIG. 1, 90% or more of bortezomib bound in block copolymer composition 5 of Comparative Example 1 was released in 1 hour after the sample preparation. On the other hand, block copolymer composition 4 of Example 1 and block copolymer composition 6 of Example 2 (these block copolymer compositions are substantially polymer micelle compositions), in each of which bortezomib was bound via a linker moiety having a protective structure, exhibited drug release ratios after a lapse of 6 hours from the sample preparation of less than 30% and less than 10%, respectively, and exhibited drug release ratios after a lapse of 24 hours from the sample preparation of 50% and 24% (not shown), respectively, showing that both of the compositions remarkably suppressed the release of bortezomib. This reveals that, according to one embodiment of the present invention, a boronic acid compound such as bortezomib can be stably retained in water (e.g., under physiological conditions).

<Evaluation of Retention Property of Drug (In Vivo)>

1. Preparation of Standard Solution of Bortezomib

Bortezomib was dissolved with DMSO so as to achieve a concentration of 10 mg/mL. 100 μL, of the resultant solution were added to a mixed solution of 1 mL of DMSO, 2 mL of a 50% sucrose solution, and 6.9 mL of water for injection. Thus, a solution (10% DMSO and 10% sucrose solution) containing bortezomib at 100 μg/mL was prepared. The solution was diluted with 0.1% formic acid to prepare solutions having bortezomib concentrations of 2.5, 9.8, 39.1, 78.1, 156.3, 625, and 1,250 ng/mL. 40 μL of normal rat plasma were sampled in a microtube and then supplemented with 10 μL, of each diluted solution or 0.1% formic acid, and the mixture was lightly stirred (standard solution: 50 μL in total, plasma concentration: 80%, 0, 0.5, 1.95, 7.81, 15.63, 31.25, 125, and 250 ng/mL in terms of bortezomib). To the resultant solution were added 150 μL of acetonitrile, and the mixture was stirred at room temperature for about 10 seconds to precipitate plasma protein. The resultant was centrifuged at about 4° C. at 10,000 rpm for about 10 minutes, and 100 μL of the supernatant were transferred to a plastic vial for HPLC as a standard solution.

2. Preparation of Measurement Sample

The drug was administered into the tail vein of Crlj:WI rats (male, 6-week-old, CHARLES RIVER LABORATORIES JAPAN, INC.). The rats were divided into two groups consisting of: a control group (administration of a 100 μg/mL bortezomib aqueous solution, n=3); and a group to which block copolymer composition 6 (polymer micelle composition) of Example 2 was administered (n=3). The dosage was 100 μg/kg in terms of bortezomib for each of the groups. The administration of block copolymer composition 6 of Example 2 was carried out with a solution (10% DMSO and 10% sucrose solution, bortezomib concentration: 100 μg/mL) of the copolymer composition. Blood was collected 5 minutes, 1 hour, 3 hours, and 6 hours after the administration to obtain plasma samples. The resultant plasma samples were cryopreserved at −80° C. for a period of time before the measurement of the bortezomib concentration.

10 μL of 0.1% formic acid were added in a microtube, 40 μL of each of the plasma samples were added, and then the mixture was lightly stirred (sample solution: 50 μL in total, plasma concentration: 80%). To the resultant solution were added 150 μL of acetonitrile, and the mixture was stirred at room temperature for about 10 seconds to precipitate plasma protein. The resultant was centrifuged at about 4° C. at 10,000 rpm for about 10 minutes, and 100 μL of the supernatant were transferred to a plastic vial for HPLC as a measurement sample. It should be noted that the plasma sample estimated to have a high free bortezomib concentration was diluted with normal rat plasma in advance to prepare a measurement sample according to the above-mentioned method.

3. Measurement of Bortezomib Concentration

Figure 2:
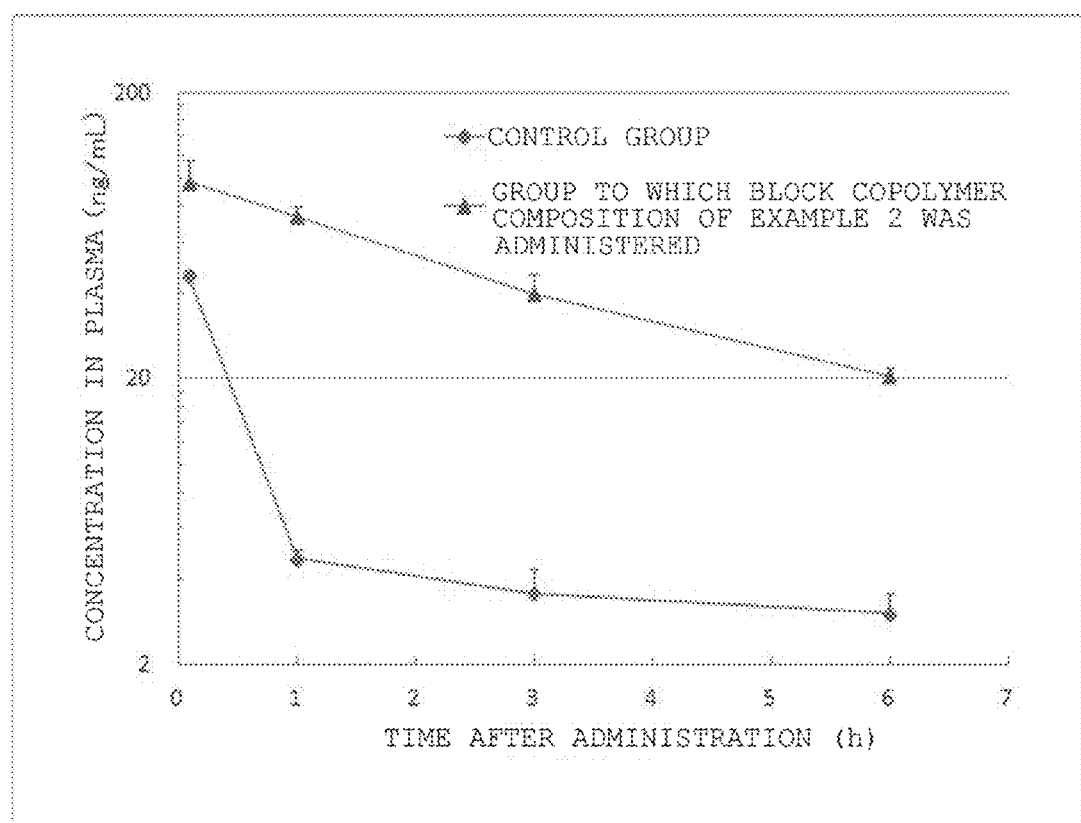
FIG. 2 is a graph showing concentrations of bortezomib in plasma of rats to which the polymer micelle composition formed of the block copolymer composition of Example 2 and a bortezomib aqueous solution were administered, respectively.

10 μL of the measurement sample were injected into an LC/MS/MS, and the concentration of free bortezomib in plasma was measured under the conditions shown in Table 1. FIG. 2 shows the results.

TABLE 1

| | | | | | |
|---|---|---|---|---|---|
| LC | LC apparatus | Product available from DIONEX under product name "UltiMate3000 LC System" | | | |
| | Column | Waters: Atlantis T3 Column, 2.1 × 100 mm, 3 μm | | | |
| | Mobile phase | A: 0.1% formic acid | | | |
| | | B: acetonitrile containing 0.1% formic acid | | | |
| | | | Time [min] | A [%] | B [%] |
| | Gradient | | 0 | 70 | 30 |
| | | | 5 | 5 | 95 |
| | | | 10 | 5 | 95 |
| | | | 10.5 | 70 | 30 |
| | | | 15 | 70 | 30 |
| | Flow rate [μL/min] | 300 | | | |
| | Column temperature [° C.] | 45 | | | |
| | Sample temperature [° C.] | 10 | | | |
| | Injection amount [μL] | 10 | | | |
| MS | MS/MS apparatus | Product available from AB SCIEX under product name "API2000 LC/MS/MS System" | | | |
| | Ion Source | TurboIonSpray ™ Ion Source (ESI) | | | |
| | Mode | MRM | | | |
| | Temperature [° C.] | 500 | | | |
| | Polarity | Positive | | | |
| | IonSpray Voltage [V] | 2,000 | | | |
| | Monitoring Time [min] | 15 | | | |
| | MRM Transition (BTZ) | Q1(Da): 367.250, Q3(Da): 226.200 | | | |

As shown in FIG. 2, the group to which the block copolymer composition of Example 2 was administered maintained a concentration of free bortezomib in plasma about 16 times as high as that of the control group 1 hour after the administration, and maintained concentrations of free bortezomib in plasma about 11 times and about 7 times as high as those of the control group even 3 hours and 6 hours after the administration, respectively. The results reveal that the block copolymer composition of Example 2 can stably retain bortezomib in blood and may be used as a pharmaceutical composition having an excellent sustained-release property.

<Drug Efficacy Test>

Figure 3A:
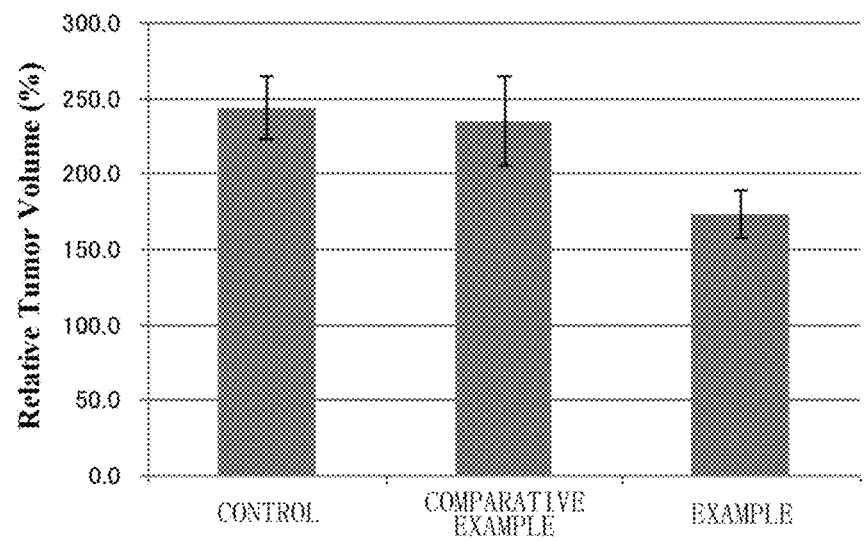
FIG. 3A is a bar graph showing relative values of tumor volumes 7 days after administration to tumor volumes on the administration date in mice to which the polymer micelle composition formed of the block copolymer composition of Example 1, the bortezomib aqueous solution, and a control solution were administered, respectively.
Figure 3B:
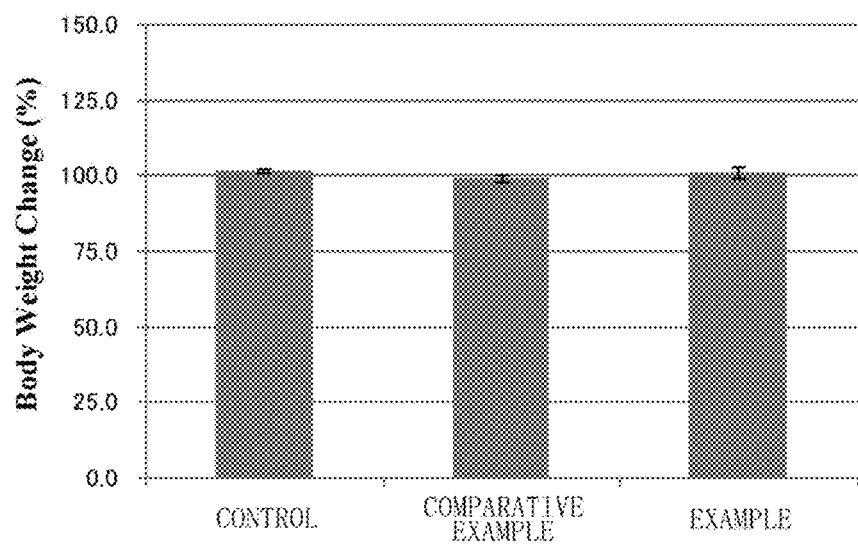
FIG. 3B is a bar graph showing relative values of body weights 7 days after administration to body weights on the administration date in mice to which the polymer micelle composition formed of the block copolymer composition of Example 1, the bortezomib aqueous solution, and the control solution were administered, respectively.

Human prostate cancer PC-3 cells were inoculated under the dorsal skin of male nude mice (Balb nu/nu, 5-week-old, CHARLES RIVER LABORATORIES JAPAN, INC.) at $3\times10^6$ cells per mouse. At the time when the tumor volume reached 90.7±4.5 mm$^3$ (mean±standard error (SE)) (on day 10 after the inoculation), the drug was administered into the tail vein. The mice were divided into the following three groups (n=6, provided that n=10 for the control group): (1) a group to which a control solution (10% sucrose/1% DMSO) was administered; (2) a group to which a bortezomib aqueous solution was administered (1 mg/kg) (Comparative Example 2); and (3) a group to which the block copolymer composition (polymer micelle composition) of Example 1 was administered (0.3 mg/kg). It should be noted that the dosage is the amount in terms of the drug for each of the groups. FIG. 3A shows the relative values of the tumor volumes after 7 days from the administration date to the tumor volumes on the administration date, and FIG. 3B shows the relative values of the body weights after 7 days from the administration date to the body weights on the administration date. As is apparent from FIG. 3A, according to the block copolymer composition (polymer micelle composition) of Example 1, the increase in tumor volume was remarkably suppressed as compared to Comparative Example 2 and the control group. FIG. 3B revealed that there was no significant difference in mouse body weight. It should be noted that, when the dosage of the bortezomib aqueous solution was set to more than 1 mg/kg, toxicity due to the active pharmaceutical ingredient became remarkable and the amount of body weight loss reached a severe level (e.g., a loss of 20% or more).

As was described above, according to one embodiment of the present invention, a boronic acid compound such as bortezomib can be stably retained in water (e.g., under physiological conditions) for a long period of time. Hence, an excellent anti-tumor effect of the boronic acid compound is provided while side effects thereof are reduced.

The invention claimed is:

1. A pharmaceutical composition comprising a block copolymer having the following chemical structure:

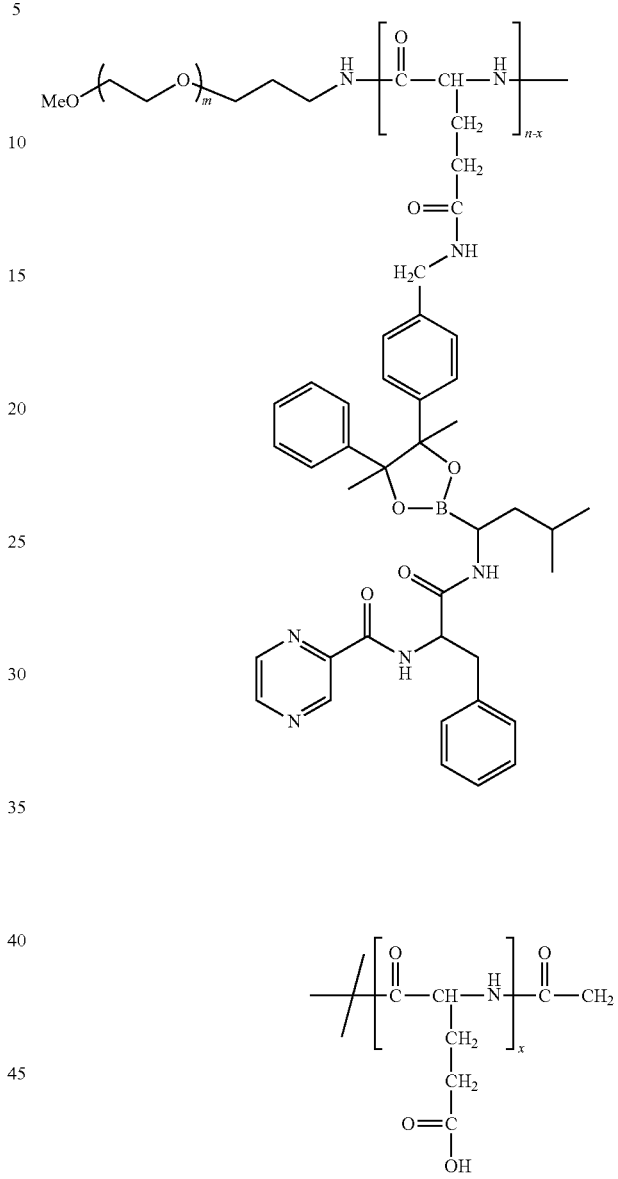

wherein:

m is an integer of 40-500;

n is an integer of 20-80;

x is an integer of 0-79 with the proviso that x is less than n;

the n-x groups and the x groups are arranged in a random sequence.

2. The pharmaceutical composition according to claim 1 having the following chemical structure:

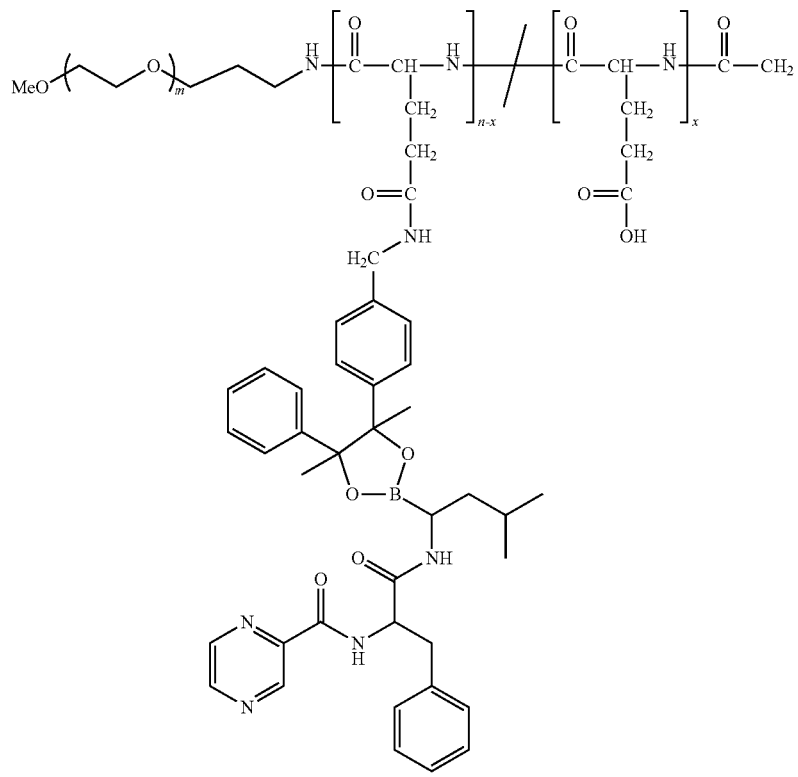
wherein:
m is 161;
n is 40;
x is 30.
3. A pharmaceutical composition having the following chemical structure:
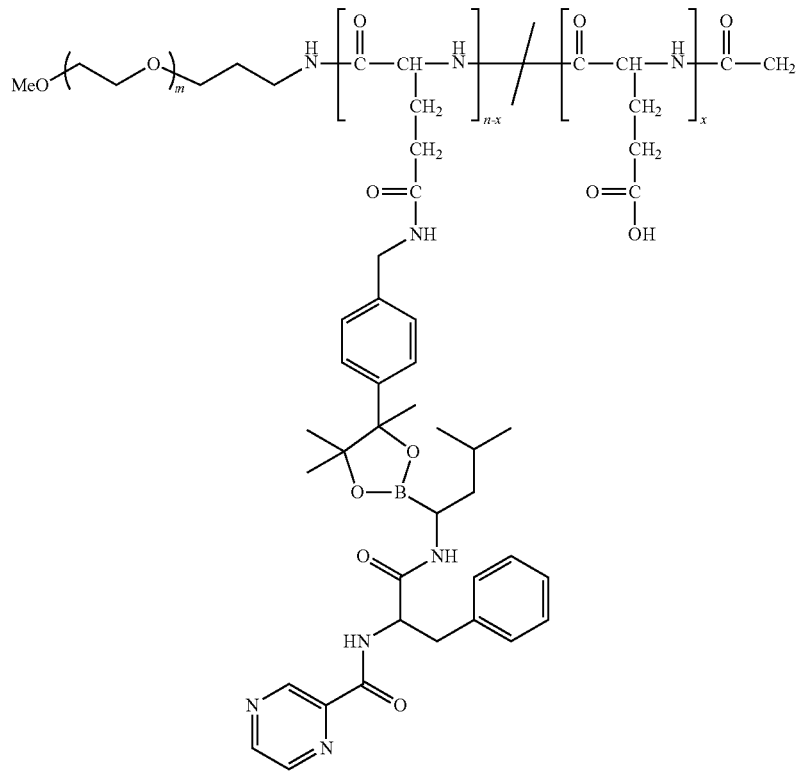

wherein:
m is 161;
n is 40;
x is 11; and
the n-x groups and the x groups are arranged in a random sequence.

* * * * *